(12) United States Patent
Holtwick et al.

(10) Patent No.: US 10,967,126 B2
(45) Date of Patent: *Apr. 6, 2021

(54) JOINING TECHNOLOGY OF A DISPENSE INTERFACE

(71) Applicant: Sanofi-Aventis Deutschland GmbH, Frankfurt am Main (DE)

(72) Inventors: Marc Holtwick, Frankfurt am Main (DE); James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,580

(22) Filed: Nov. 2, 2018

(65) Prior Publication Data

US 2019/0175834 A1   Jun. 13, 2019

Related U.S. Application Data

(63) Continuation of application No. 14/114,266, filed as application No. PCT/EP2012/057696 on Apr. 26, 2012, now Pat. No. 10,117,994.

(Continued)

(30) Foreign Application Priority Data

Jul. 8, 2011   (EP) .................................... 11173284

(51) Int. Cl.
*A61M 5/19* (2006.01)
*A61M 5/20* (2006.01)
(Continued)

(52) U.S. Cl.
CPC ................ *A61M 5/19* (2013.01); *A61M 5/20* (2013.01); *B65D 11/20* (2013.01);
(Continued)

(58) Field of Classification Search
CPC ...... A61M 5/19; A61M 5/20; A61M 5/31546; A61M 5/344; A61M 5/345;
(Continued)

(56) References Cited

U.S. PATENT DOCUMENTS 533,575 A    2/1895  Wilkens
2,615,446 A *  10/1952 Lingenfelter ......... A61M 5/282
                                                    604/212

(Continued)

FOREIGN PATENT DOCUMENTS

EP   0937471 A2   8/1999
EP   0937476 A2   8/1999
(Continued)

OTHER PUBLICATIONS

Communication of a Notice of Opposition issued in European Patent Application No. 12717698.0, dated Jan. 14, 2016 (28 pages).
(Continued)

*Primary Examiner* — Theodore J Stigell
(74) *Attorney, Agent, or Firm* — McCarter & English, LLP

(57) ABSTRACT

The present disclosure relates to an apparatus and a method. The apparatus comprises a body part and a cover part, wherein the body part and the cover part are configured to at least partially form a fluid channel between a surface of the body part and a surface of the cover part. The surfaces of the body part and the cover part may be facing surfaces. The method comprises manufacturing the apparatus according to the present disclosure.

15 Claims, 14 Drawing Sheets

Related U.S. Application Data

(60) Provisional application No. 61/480,063, filed on Apr. 28, 2011.

(51) Int. Cl.
  *B65D 6/00* (2006.01)
  *A61M 5/315* (2006.01)
  *A61M 5/34* (2006.01)
  *A61M 5/50* (2006.01)
  *A61M 5/24* (2006.01)
  *A61M 5/31* (2006.01)

(52) U.S. Cl.
  CPC ......... *A61M 5/31546* (2013.01); *A61M 5/344* (2013.01); *A61M 5/345* (2013.01); *A61M 5/50* (2013.01); *A61M 2005/2407* (2013.01); *A61M 2005/2474* (2013.01); *A61M 2005/2496* (2013.01); *A61M 2005/3128* (2013.01); *A61M 2205/273* (2013.01)

(58) Field of Classification Search
  CPC .. A61M 2005/2407; A61M 2005/2474; A61M 5/282; A61M 5/50; A61M 2005/2496; A61M 2005/3128; A61M 2205/273; B65D 11/20
  See application file for complete search history.

(56) References Cited

U.S. PATENT DOCUMENTS

| | | | |
|---|---|---|---|
| 2,646,044 A * | 7/1953 | Diack | A61M 3/0245 604/262 |
| 2,687,727 A * | 8/1954 | Lawshe | A61M 5/282 604/204 |
| RE26,006 E * | 4/1966 | Gewecke | A61M 5/155 604/142 |
| 4,044,757 A | 8/1977 | McWhorter et al. | |
| 4,978,336 A | 12/1990 | Capozzi et al. | |
| 5,226,895 A | 7/1993 | Harris | |
| 5,279,586 A | 1/1994 | Balkwill | |
| 5,286,258 A | 2/1994 | Haber et al. | |
| 5,304,152 A | 4/1994 | Sams | |
| 5,320,609 A | 6/1994 | Haber et al. | |
| 5,378,233 A * | 1/1995 | Haber | A61M 5/19 604/135 |
| 5,383,865 A | 1/1995 | Michel | |
| 5,478,323 A | 12/1995 | Westwood et al. | |
| 5,480,387 A | 1/1996 | Gabriel et al. | |
| 5,505,704 A * | 4/1996 | Pawelka | A61M 5/19 604/191 |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 8,100,295 B2 | 1/2012 | Keller | |
| 10,117,994 B2 * | 11/2018 | Holtwick | A61M 5/19 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0086457 A1 | 4/2006 | Ohshita et al. | |
| 2006/0153693 A1 | 7/2006 | Fiechter et al. | |
| 2007/0221321 A1 * | 9/2007 | Bohm | B23K 26/18 156/272.8 |
| 2008/0154192 A1 | 6/2008 | Schraga | |
| 2009/0275916 A1 | 11/2009 | Harms et al. | |
| 2010/0075077 A1 * | 3/2010 | Bicker | C03C 17/30 428/34.6 |
| 2012/0302986 A1 | 11/2012 | Brem et al. | |
| 2013/0023833 A1 | 1/2013 | Kayser | |
| 2014/0054295 A1 | 2/2014 | Holtwick et al. | |

FOREIGN PATENT DOCUMENTS

| | | |
|---|---|---|
| EP | 2335755 A1 | 6/2011 |
| JP | H08-503874 A | 4/1996 |
| JP | 2011-5182 A | 1/2011 |
| WO | 1999/38554 A1 | 8/1999 |
| WO | 2001/10484 A1 | 2/2001 |
| WO | 2007/109915 A1 | 10/2007 |
| WO | 2007/131371 A1 | 11/2007 |
| WO | 2008/083037 A1 | 7/2008 |
| WO | 2011/091542 A1 | 8/2011 |
| WO | 2011/116484 A1 | 9/2011 |
| WO | 2012/110474 A1 | 8/2012 |

OTHER PUBLICATIONS

English Translation of Notice of Reason(s) for Rejection issued in the Japanese Office Action for Application No. 2014-506881, dated Feb. 23, 2016 (12 pages).

English Translation of Notice of Reason(s) for Rejection issued in the Japanese Office Action for Application No. 2014-506881, dated Jan. 31, 2017 (14 pages).

English Translation of Japanese Office Action/Decision for Refusal from corresponding Japanese Patent App. No. 2014-506881, dated Jan. 9, 2018 (4 pages).

\* cited by examiner

JOINING TECHNOLOGY OF A DISPENSE INTERFACE

CROSS-REFERENCE TO RELATED APPLICATIONS

The present application is a continuation of U.S. patent application Ser. No. 14/114,266, filed Oct. 28, 2013, which is a U.S. National Phase Application pursuant to 35 U.S.C. § 371 of International Application No. PCT/EP2012/057696 filed Apr. 26, 2012, which claims priority to U.S. Provisional Patent Application No. 61/480,063, filed Apr. 28, 2011 and European Patent Application No. 11173284.8 filed Jul. 8, 2011. The entire disclosure contents of these applications are herewith incorporated by reference into the present application.

FIELD OF INVENTION

The present patent application inter alia relates to medical devices for delivering at least two drug agents from separate reservoirs. Such drug agents may comprise a first and a second medicament. The medical device includes a dose setting mechanism for delivering the drug agents automatically or manually by the user.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections. The present invention inter-alia faces the technical problem of providing a dispense interface, dose dispenser and/or drug delivery device allowing a simple manufacturing thereof.

According to the present invention, an apparatus comprises a body part and a cover part, wherein the body part and the cover part are configured to at least partially form a fluid channel between a surface of the body part and a surface of the cover part. In particular, the surfaces of the body part and the cover part may be facing surfaces.

According to the present invention, a method comprises manufacturing the apparatus according to the present invention.

The apparatus may be a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day.

For instance, the apparatus is a medical device configured to eject at least two drug agents from separate reservoirs comprising a first and a second medicament, respectively, but it is not limited thereto. Alternatively, the medical device is for instance a conventional medical device configured to eject a drug agent from a single reservoir such as Applicant's Solostar insulin injection pen.

Alternatively, the apparatus may be a disposable part attachable to a medical device such as a drug delivery device. For instance, the apparatus is a dispense interface attachable to a medical device configured to eject a drug agent. A dispense interface may be configured to be in fluid communication with at least one reservoir of the medical device containing at least one medicament. For instance, the dispense interface is a type of outlet that allows the at least one medicament to exit the medical device.

The fluid channel may provide a fluid connection between at least one inlet and one outlet of the fluid channel. The inlet and the outlet, respectively may be either arranged in at least one of the body part and the cover part or between the surfaces of the body part and the cover part. For instance, the fluid channel provides a fluid connection between a first inlet and a second inlet, respectively, and an outlet. For instance, the fluid channel is at least partially Y-like, T-like or Z-like shaped.

The fluid channel may extend in a plane. Also, the fluid channel may have a more complex geometry. In particular, the fluid channel may extend in at least two angled planes.

The diameter of the fluid channel may be between 0.01 mm and 10 mm. In particular, the diameter of the fluid channel may be between 0.1 mm and 1 mm, for instance about 0.3 mm. The ratio between the length of the fluid channel and the diameter of the fluid channel (length:diameter ratio) may be substantially large, for instance between 10:1 and 1000:1. In particular, the length:diameter ratio may be between 20:1 and 100:1, for instance about 33:1 or 66:1. The length of the fluid channel may preferably describe the longest fluid communication path of the fluid channel.

The body part and the cover part may be joining components of the apparatus. The body part and the cover part may be any three-dimensional structure. For instance, the body part defines an inner body of the apparatus and/or the cover part defines a manifold of the apparatus. For instance, the body part and the cover part are joined, when the apparatus is manufactured (e.g. assembled). The joined body part and cover part may be fitted with further components of the apparatus.

The body part and the cover part may be configured to be joined at least at a joining area of the surfaces of the body part and the cover part. The surfaces of the body part and the cover part may face each other, when the body part and the cover part are joined. For instance, the joining area of the surfaces of the body part and the cover part is a circumferential area, for instance a ring-like area. For instance, the joining area of the surfaces extends along an outer edge of at least one of the body part and the cover part, for instance an outer edge of the surface of the cover part and/or the body part. When the body part and the cover are joined, the joining area of the surfaces of the body part and the cover part may enclose a non-contact area between the body part and the cover part.

The joining area may be a mating surface area of the surfaces of the body part and the cover part or a part of a mating surface area of the surfaces of the body part and the cover part. When the body part and the cover are joined, the mating surface area of the surfaces of the body part and the cover part may be defined by a contact area between the body part and the cover part.

The body part and the cover part may be joined by a material connection, for instance by welding such as friction welding, ultrasonic welding and laser welding, vulcanization and/or glueing. For instance, the joining area of the surfaces of the body part and the cover part is defined by a welding track, a vulcanizing area and/or a glueing area, respectively.

The surfaces of the body part and the cover part (between which the fluid channel is at least partially formed) may be vertically oriented. Vertically oriented is preferably to be understood such that at least a (e.g. continuous) part of these surfaces is at least substantially parallel to a longitudinal axis of the apparatus. For instance, the joining area of these surfaces may be at least substantially parallel to a longitudinal axis of the apparatus. For instance, the longitudinal axis of the apparatus may be a vertical centerline of the apparatus. For instance, the vertically oriented surfaces may at least partially include an angle of less than 30°, preferably less than 10° with the longitudinal axis of the apparatus. For instance, a predominant part of these surfaces may include an angle of less than 30°, preferably less than 10° with the longitudinal axis of the apparatus. For instance, the joining area of these surfaces may include an angle of less than 30°, preferably less than 10° with the longitudinal axis of the apparatus.

Vertical orientation of the surfaces of the body part and the cover part (between which the fluid channel is at least partially formed) is inter alia advantageous to allow the body part and the cover part to be joined in an at least substantially vertical plane which is easy accessible (e.g. for a joining tool). For instance, these surfaces may accordingly be joined at a vertically oriented joining area by laser welding by a laser positioned angled or perpendicular to the longitudinal axis of the apparatus. This is for instance advantageous, because from such a lateral position the laser may only need to pass through the cover part which may have an at least substantially uniform thickness at the joining area. In contrast to this, from a longitudinal position, the laser may typically need to pass through additional components at least partially covering the cover part resulting in undesired scattering and attenuation of the laser beam.

The body part and the cover part are configured to at least partially form the fluid channel between the surfaces of the body part and the cover part. In particular, the body part and the cover part may be configured to at least partially form the fluid channel between facing surfaces of the body part and the cover part. For instance, the fluid channel is at least partially defined by a cavity at a non-contact area of the surfaces of the body part and the cover part, when the body part and the cover part are joined.

For instance, a groove arrangement is arranged in the surface of the body part (or the cover part). When the body part and the cover part art joined, the groove arrangement may at least partially be covered by the surface of the cover part (or the body part) such that a cavity is formed at least partially defining the fluid channel. In particular, the surface of the cover part (or the body part) may cover the groove perpendicular to a longitudinal direction of the groove. The groove arrangement may also be arranged in the surface of the body part and/or the surface of the cover part.

The geometry of the surfaces of the body part and the cover part may at least partially be defined by the geometry of the fluid channel. For instance, if the fluid channel at least substantially extends in a plane, the surfaces of the body part and the cover part may be defined by this plane and may be at least substantially flat. However, if the geometry of the fluid channel is more complex, the geometry of the surfaces of the body part and the cover part may be also more complex. For instance, if the fluid channel extends in at least two angled planes, the geometry of the surfaces of the body part and the cover part may have a 3-dimensional structure, at least partially defined by the at least two angled planes.

Parts having fluid channels with a large length:diameter ratio and/or a complex geometry cannot be simply manufactured, for instance by moulding such as injection moulding. Complex tooling is necessary to manufacture such parts.

However, the body part and the cover part according to the present invention can be simply manufactured, for instance by moulding such as injection moulding, for instance by use of an open-and-shut tool without the need for complex tooling. By joining the body part and the cover part after manufacturing thereof, it is thus possible to form a joined part having fluid channels with a high length:diameter ratio and/or a complex geometry and/or tight tolerances.

The present invention is therefore inter alia advantageous to allow a simple manufacturing of the apparatus according to the present invention.

In the following, features and embodiments (exhibiting further features) of the present invention will be described, which are understood to equally apply to the apparatus and the method as described above. These single features/embodiments are considered to be exemplary and non-limiting, and to be respectively combinable independently from other disclosed features/embodiments of the apparatus and the method as described above. Nevertheless, these features/embodiments shall also be considered to be disclosed in all possible combinations with each other and with the apparatus and the method as described above. For instance, a mentioning that an apparatus according to the present invention is configured to perform a certain action should be understood to also disclose an according method step of the method according to the present invention.

According to an embodiment of the present invention, the body part comprises a recess and a first body part reservoir and/or a second body part reservoir, wherein the fluid channel provides a fluid connection from the first body part reservoir and/or the second body part reservoir to the recess. For instance, the recess defines an outlet of the fluid channel, and the first and second body part reservoir define a first and second inlet of the fluid channel, respectively.

The recess may be configured to at least partially receive one proximal end of a needle of a dose dispenser and to reside in fluid connection with the needle of the dose dispenser. For instance, the dose dispenser is a standard needle assembly or a double-ended needle assembly. For instance, a distal end of the needle is inserted into a desired injection site before an injection.

The first and second body part reservoir may be configured to be in fluid connection with a respective fluid reservoir. For instance, a first and second piercing needle ends in the first and second body part reservoir, respectively. In particular, the first and second piercing needles may be configured to pierce a septum of a respective fluid reservoir such as a medicament reservoir, cartridge and/or a container, to reside in fluid connection with the fluid reservoir and provide a fluid communication between the respective fluid reservoir and the first and second body part reservoir. The first and second body part reservoir may at least partially form a valve chamber, for instance the first and second body part are configured to at least partially receive a diaphragm of a diaphragm valve.

For instance, the apparatus is a dispense interface providing a fluid connection from a first and second fluid reservoir of a drug delivery device to a needle assembly of a dispense interface, for instance the apparatus provides the fluid connection via the first and second body part reservoir, the fluid channel and the recess. For instance, the fluids from the first and second fluid reservoir enter the fluid channel via a respective first and second diaphragm valve at least partially arranged in the respective first and second body part reservoir.

According to an embodiment of the present invention, at least one of the first and/or second body part reservoirs is configured to receive a diaphragm valve such that the diaphragm valve is at least substantially arranged in a first plane parallel to a longitudinal axis of said apparatus. For instance, the first and second body part reservoir are configured to receive a first and second diaphragm valve, respectively, such that the first and second diaphragm valve are at least substantially arranged in a first plane parallel to a longitudinal axis of the apparatus.

Something may be understood to be arranged or at least substantially arranged in a plane, if it is cut by the plane and/or a longitudinal axis (e.g. an axis along the direction of the largest extension) thereof is coplanar or at least substantially coplanar with the plane. A longitudinal axis is for instance substantially coplanar with a plane, if the longitudinal axis includes an angle of less than 30°, preferably less than 10° with the plane.

As described above, the first and second body part reservoir may at least partially form a valve chamber for a first and second diaphragm valve. For instance, a first and second diaphragm valve may at least partially be received in the first and second body part reservoir, respectively.

The diaphragm valve is at least substantially arranged in the first plane. For instance, the diaphragm of the diaphragm valve is at least partially received in one of the first and/or second body part reservoir such that the first plane cuts the diaphragm valve. For instance, a longitudinal axis of the diaphragm valve is at least substantially coplanar with the first plane. For instance, a symmetry axis, such as a rotational axis of the diaphragm valve is angled to the first plane, for instance the symmetry axis includes an angle equal to or greater than 60°, preferably 80° with the first plane. In particular, the symmetry axis may be perpendicular to the first plane and/or to a surface of the diaphragm valve facing the body part and/or the cover part.

The diaphragm valve may be at least substantially flat. Something may be understood to be substantially flat, if the diameter thereof in direction of the longitudinal axis is at least twice of the thickness thereof in perpendicular direction of the longitudinal axis. For instance, the diaphragm of the diaphragm valve has a generally convex shape. A symmetry axis of the generally convex shaped diaphragm may be a centerline running through the apex thereof; the longitudinal axis of the generally convex shaped diaphragm may be perpendicular to the symmetry axis.

The longitudinal axis of the apparatus may be a vertical centerline of the apparatus such that, for instance the first plane is a vertical plane. For instance, the first plane is at least partially coplanar with the joining area of the surfaces of the body part and the cover part. The first plane may be spaced from the longitudinal axis of the apparatus. For instance, the first plane is spaced from, but parallel to a symmetry plane of the apparatus. Alternatively or additionally, the first plane may be perpendicular to a symmetry plane of the apparatus. The first plane may laterally cut the apparatus, for instance the first plane is a lateral plane parallel to a symmetry plane of the apparatus. For instance, a symmetry plane of the apparatus is coplanar with the longitudinal axis of the apparatus. For instance, the first and/or second body part reservoir and/or the first and/or second piercing needle may be arranged in a symmetry plane of the apparatus. The symmetry plane may cut the first and second body part reservoir. The symmetry plane may be coplanar with the longitudinal axis of the first and second piercing needle.

This embodiment is inter alia advantageous to allow arranging the body part and the cover part such that the fluid channel may be formed at least partially in a lateral plane parallel to the first plane. Furthermore, it is inter alia advantageous to allow the body part and the cover part to be joined in a lateral plane parallel to the first plane, for instance by laser welding by a laser laterally positioned, for instance angled or perpendicular to the first plane. Laterally positioning the laser is for instance advantageous, because from such a lateral position the laser may only need to pass through the cover part which may have an at least substantially uniform thickness at the joining area. In contrast to this, from a longitudinal position, for instance perpendicular to the first plane, the laser may typically need to pass through additional components at least partially covering the cover part resulting in undesired scattering and attenuation of the laser beam. In other words, this embodiment is inter alia advantageous to allow the body part and the cover part to be joined at a joining area of surfaces of the body part and the cover part which is easily accessible by a laser.

According to an embodiment of the present invention, at least one of the body part and the cover part comprises a groove arrangement, the groove arrangement arranged in the surface of the at least one of the body and the cover part.

For instance, the groove arrangement is a fluid groove arrangement. The groove arrangement may comprise any number of grooves, which may be any indentations on the surface of the respective part which permits the passing of fluid along the surface thereof.

According to an embodiment of the present invention, the body part defines an inner body of the apparatus and the cover part defines a manifold of the apparatus.

According to an embodiment of the present invention, at least one of the body part and the cover part is formed by moulding.

In particular, at least one of the body part and the cover part is formed by injection moulding. For instance, at least one of the body part and the cover part is formed by moulding by use of an open-and-shut tool.

For instance, use of an open-and-shut tool reduces the need for fragile core pins or split lines with a groove arrangement. This also allows for relatively complex and tight tolerance geometry without complex tooling. The moulding of key assembly snap features on the same component, such as an outer protrusion on the body part, may also helps reduce tolerance stack-ups and also tends to allow for small needle wells and therefore smaller ullage.

This embodiment is inter alia advantageous to allow a simple manufacturing of the body part and the cover part without need for complex tooling and/or to reduce the ullage.

According to an embodiment of the present invention, at least one of the body part and the cover part is formed from a Cyclo Olefin Polymer (COP) material.

COP materials are preferably used in injection moulding of the body part and the cover part respectively. COP materials have a high biocompatibility. For instance, COP materials have little to no extractables and most COP materially can undergo sterilization by gamma radiation, steam and/or ethylene oxide.

This embodiment is inter alia advantageous to allow a simple manufacturing of the body part and the cover part from a biocompatible material.

According to an embodiment of the present invention, surfaces of the body part and the cover part are at least substantially flat at a joining area, for instance the joining area described above. For instance, the joining area of the surfaces extends along an outer edge of at least one of the body part and the cover part, for instance an outer edge of the surface of the cover part.

The joining area of the surfaces may be an at least substantially flat circumferential area which may enclose a 3-dimensionally structured centric area. For instance, the (3-dimensional) groove arrangement is entirely arranged in the centric area such that the surfaces joined at the joining area may seal the entire groove arrangement. This embodiment is inter alia advantageous to allow a comprehensive and tight sealing of the fluid channel (e.g. the groove arrangement) by the surfaces of the body part and the cover part at the joining area.

According to an embodiment of the present invention, the surfaces of the body part and the cover part are joined by laser welding at a joining area, for instance the joining area described above. In particular, the laser welding may be a laser-transmission-welding. For instance, the laser welding track (e.g. a laser welding line) defines the joining area of the surfaces of the body part and the cover part. The laser welding track may be a closed track on the surfaces of the body part and the cover part. For instance, the laser welding track extends along an outer edge of the surface of the cover.

The welding laser may be a gas laser or a solid state laser such as a diode laser. Preferably, the welding laser may be a Pulsed Fiber Laser. The wavelength of the welding laser may be between 100 nm and 10 urn, preferably between 900 nm and 1100 nm, in particular one of 1062 nm, 1062 nm+/−3 nm or 1062 nm+/−10 nm.

This embodiment is inter alia advantageous to allow a comprehensive and tight sealing of the fluid channel.

According to an embodiment of the present invention, one of the body part and the cover part is at least partially formed from a material at least substantially transparent to radiation of a welding laser of the laser welding. For instance, the cover part may at least partially be formed from a material at least substantially transparent to radiation of the welding laser.

The material may at least substantially be transparent for radiation with a wavelength between 400 nm and 1200 nm, between 800 nm and 1200 nm, or between 1000 and 1200 nm, in particular for radiation with a wavelength of one of 1062 nm. For instance, a COP material may be at least substantially transparent for radiation at a wavelength between 400 nm and 1200 nm.

A material may be at least substantially transparent to radiation of a specific wavelength, if the material has a transmittance (i.e. the ratio of incident light passing through the part; light passed through/incident light ratio) at the specific wavelength and a thickness of 1 mm equal to or larger than 0.5:1, preferably equal to or larger than 0.8:1.

For laser transmission welding, the joining area of the surfaces of the body part and the cover part is to be accessible for a welding laser positioned perpendicular and/or angled to the joining areas. The welding laser may activate a joining area of the surfaces of the body part and the cover part. A circumferential access in the plane of the joining area of the surfaces is not necessary. For instance, the cover part may at least partially be formed from a material at least substantially optically clear to activate a joining area of the surfaces of the body part and the cover part with minimal interference, for instance a mating surface area or a part of the mating surface area residing between the two parts.

This embodiment is inter alia advantageous to allow a joining of the body part and the cover part by laser transmission welding and to minimize the design constraints for the body part and the cover part.

According to an embodiment of the present invention, a thickness of the one of the body part and the cover part is at least substantially uniform perpendicular to the surfaces of the body part and the cover part at the joining area.

The thickness of the respective part may be at least substantially uniform, if the thickness varies less than 20 percent, preferably less than 5 percent. For instance, the at least substantially uniform thickness of the respective part may be a uniform thickness between 0.1 mm and 5 mm, preferably between 0.5 mm and 2 mm. The transmittance of the respective part in a direction perpendicular to the surfaces of the body part and the cover part at the joining area may be equal to or larger than 0.5:1, preferably equal to or larger than 0.8:1.

This embodiment is inter alia advantageous to ensure an at least substantially constant transmission of the welding laser through the respective part. Furthermore, if the joining area of the surfaces of the body part and the cover part is at least substantially flat, this embodiment is inter alia advantageous to ensure an at least substantially constant focal length of the welding laser.

According to an embodiment of the present invention, at least one of the body part and the cover part is at least partially formed from a material doped with a laser welding additive. For instance, the body part is at least partially formed from a material doped with a laser welding additive.

The laser welding additive may increase the respective part's sensitivity to laser light. The laser welding additive may be carbon black. For instance, the doping concentration of the laser welding additive is at least 0.2 weight percent.

For instance, the material doped with a laser welding additive is at least substantially opaque to radiation of the welding laser. A material may be at least substantially opaque to radiation of a specific wavelength, if the material has a opacity (i.e. the ratio of incident light absorbed in the part; incident lightlight passed through ratio) at the specific wavelength and a thickness of 1 mm equal to or larger than 1:0.5, preferably equal to or larger than 1:0.2.

This embodiment is inter alia advantageous to ensure an at least substantially constant absorption of the welding laser energy at the joining area of the surfaces of the body part and the cover part and/or to allow joining the body part and the cover part by laser transmission welding.

According to an embodiment of the present invention, the apparatus is a medical device configured to eject a medicament such as a drug delivery device or the apparatus is a dispense interface attachable to a medical device configured to eject a medicament such as a drug delivery device.

According to an embodiment of the present invention, the apparatus comprises the body part defining an inner body forming the first body part reservoir and the second body part reservoir, a first piercing needle in fluid communication with the first body part reservoir, a second piercing needle in fluid communication with the second body part reservoir, the cover part defining a manifold positioned adjacent the inner body and comprising a groove arrangement, and a lockout element.

For instance, the first and second piercing needles are positioned for piercing a first and second cartridge, respectively, contained within a drug delivery device.

For instance, the lockout element is operatively disposed on a body, the lockout element comprising a first wing in a first position and a second wing in a first position such that when the dispense interface is connected and then removed from a drug delivery device, the first wing moves to a second position and the second wing moves to a second position so as to prevent the dispense interface from being reattached to a drug delivery device.

In particular, the apparatus may be a dispense interface for use with a drug delivery device. The dispense interface may comprise a main outer body and an inner body positioned within at least a portion of the main outer body. The inner body may be configured for connection to a drug delivery device and defines a first inner body reservoir and a second inner body reservoir. The dispense interface may further comprise a first piercing needle in fluid communication with the first inner body reservoir and positioned for piercing a first reservoir contained within a drug delivery device. A second piercing needle may be provided by the inner body and in fluid communication with the second inner body reservoir and positioned for piercing a second reservoir contained with a drug delivery device. A manifold may be positioned adjacent a generally flat surface of the inner body and comprises a fluid groove arrangement. A valve arrangement may be positioned between the inner body and the manifold. The valve arrangement may control fluid communication of a first fluid contained in the first cartridge and a second fluid contained in the second cartridge by way of the fluid groove arrangement to a holding chamber of the inner body. The dispense interface may further comprise a lockout preventing dispense interface reuse.

According to an embodiment of the present invention, the manufacturing comprises at least one of moulding at least one of the body part and the cover part of the apparatus, and joining by laser welding the surfaces of the body part and the cover part at a joining area.

This embodiment is inter alia advantageous to allow a simple manufacturing of the body part and cover part and a comprehensive and tight sealing of the fluid channel.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
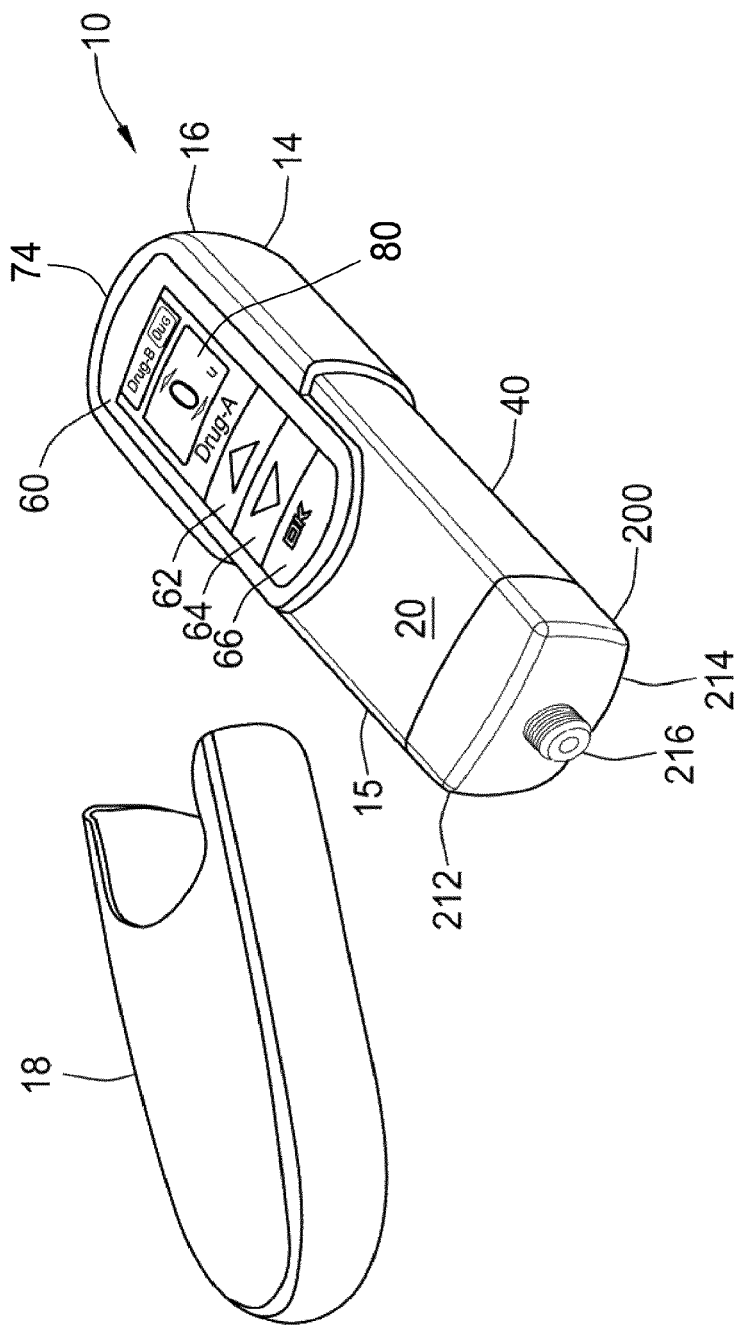
FIG. 1 illustrates a perspective view of the delivery device illustrated in FIGS. 1a and 1b with an end cap of the device removed.
Figure 2:
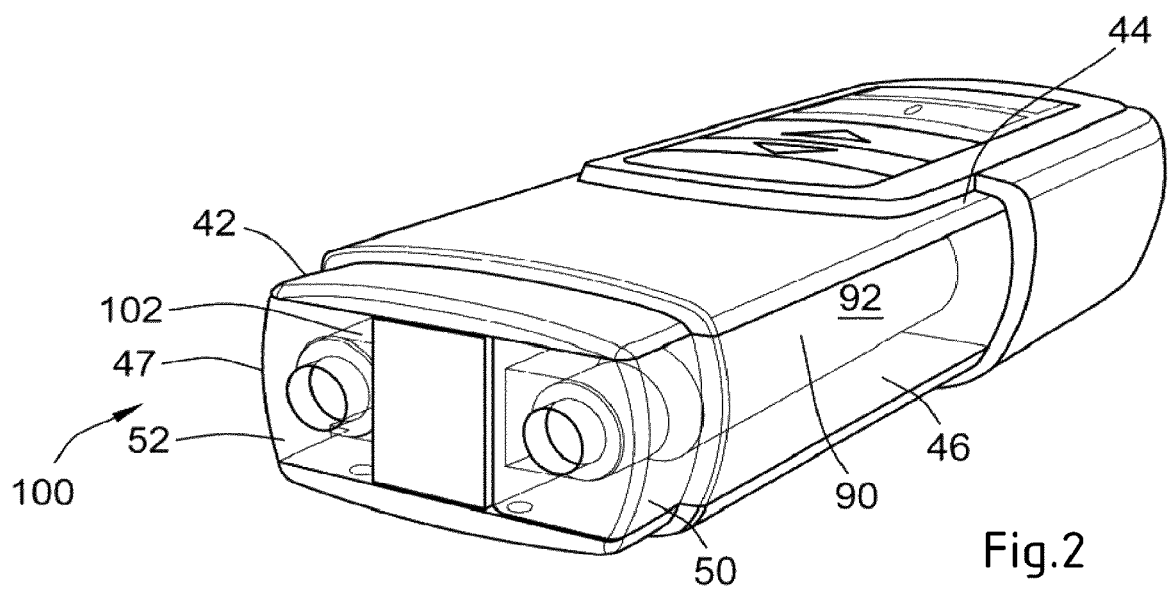
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this factional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
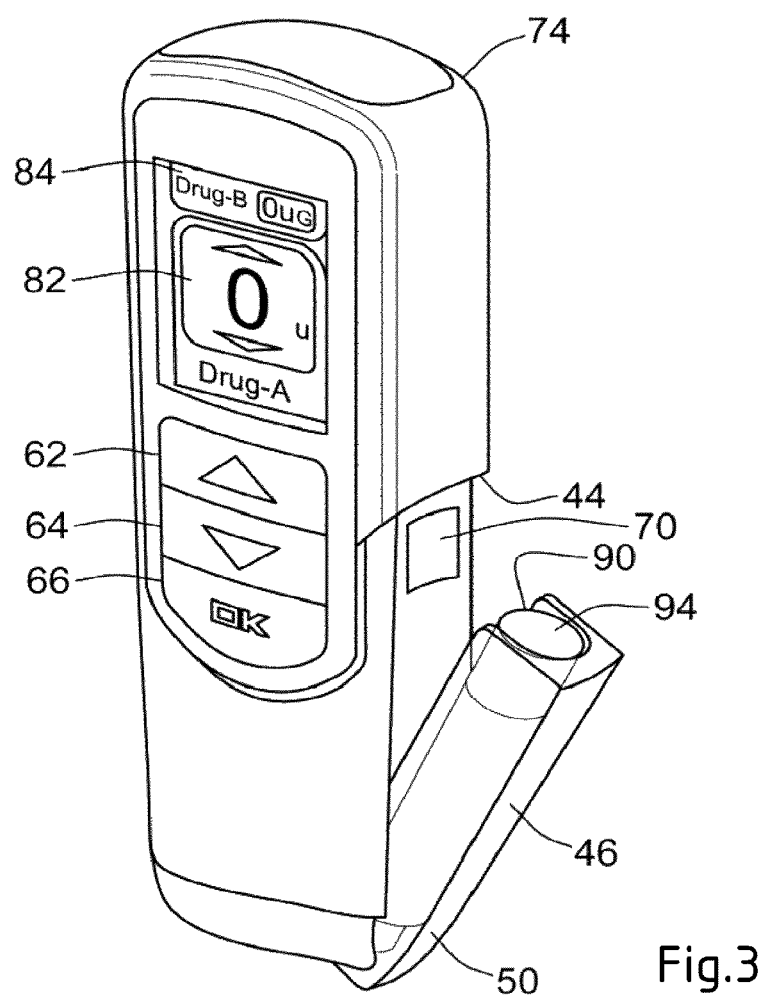
FIG. 3 illustrates a perspective view of the cartridge holder illustrated in FIG. 1 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
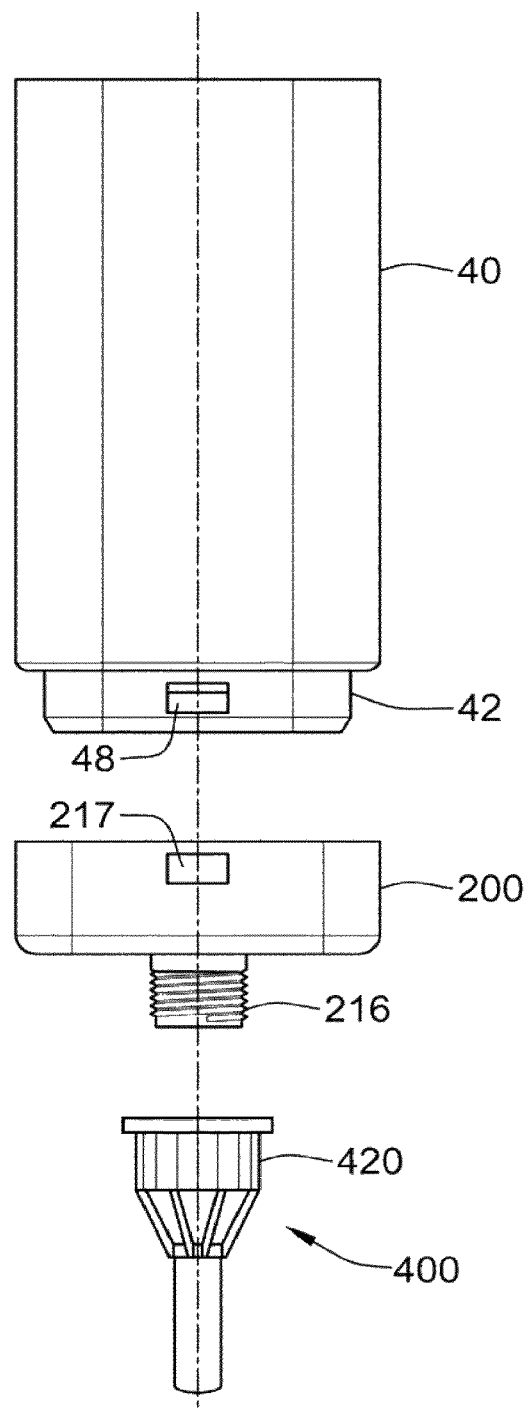
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
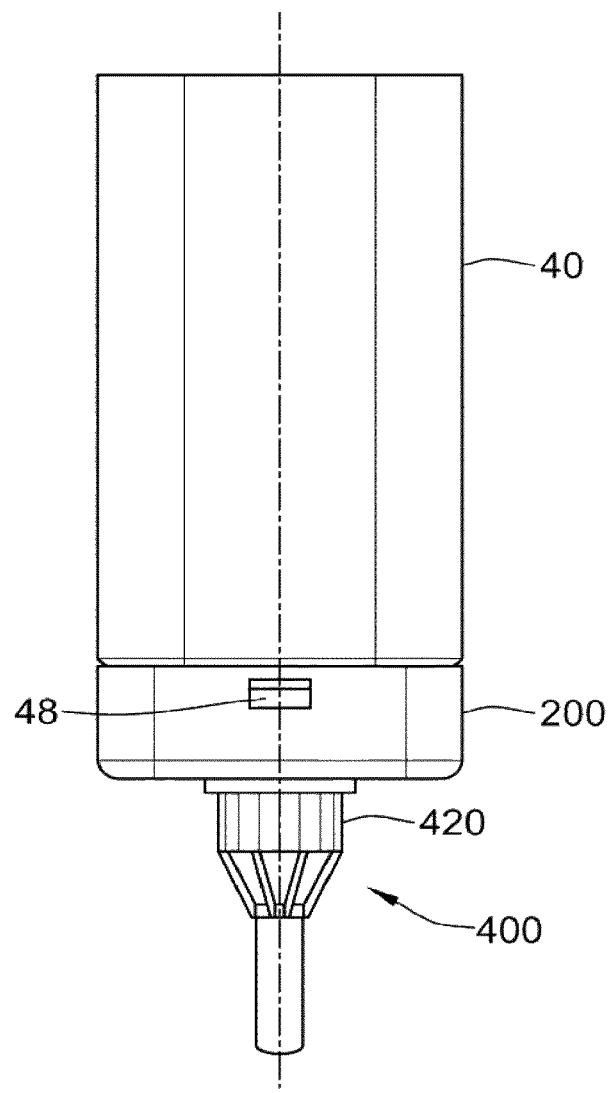
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
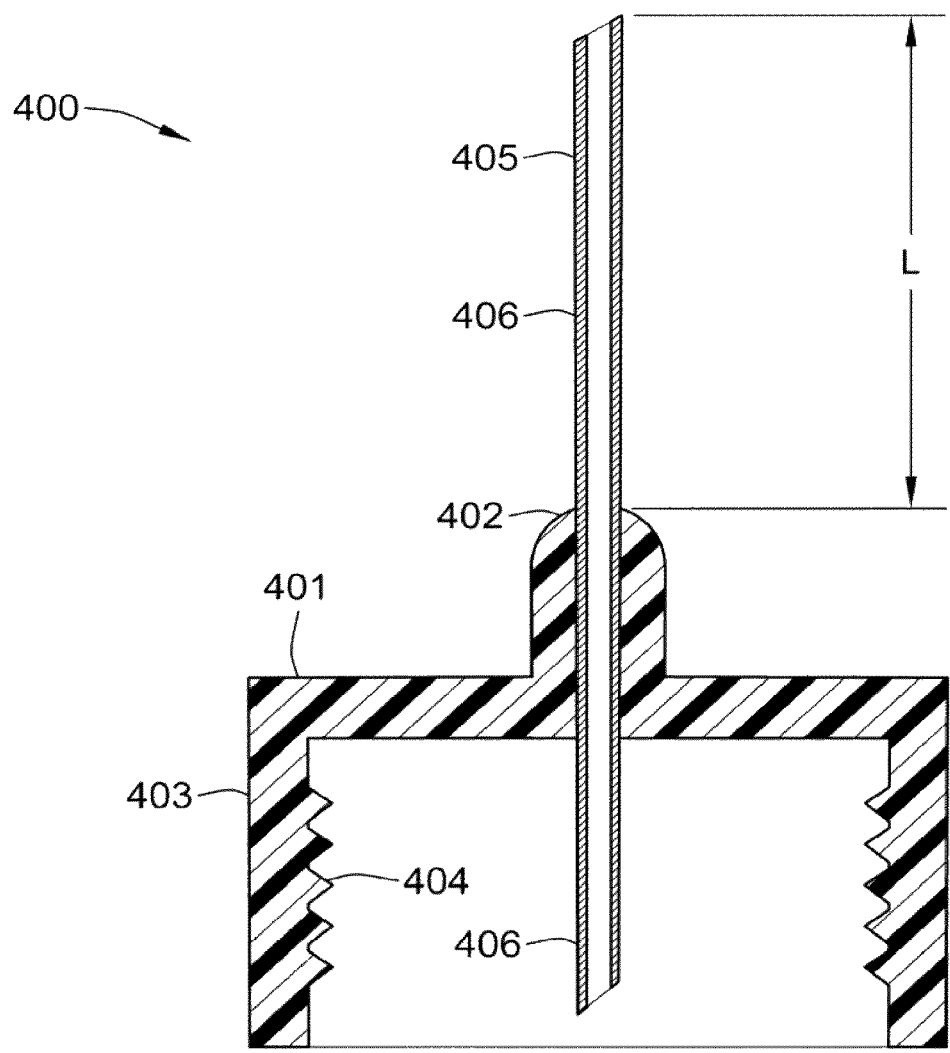
FIG. 6 illustrates one arrangement of the dose dispenser that may be mounted on a distal end of the delivery device.
Figure 7:
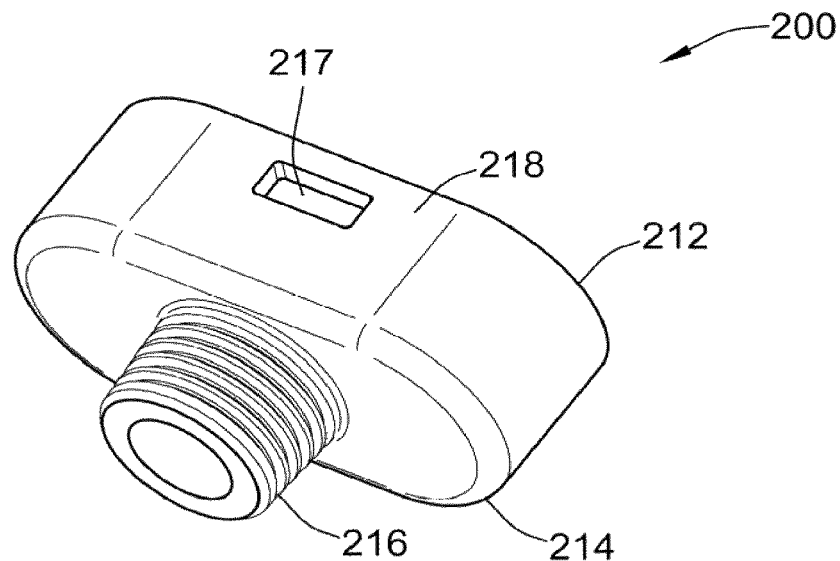
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
 a. a main outer body 210,
 b. an first inner body 220,
 c. a second inner body 230,
 d. a first piercing needle 240,
 e. a second piercing needle 250,
 f. a valve seal 260, and
 g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
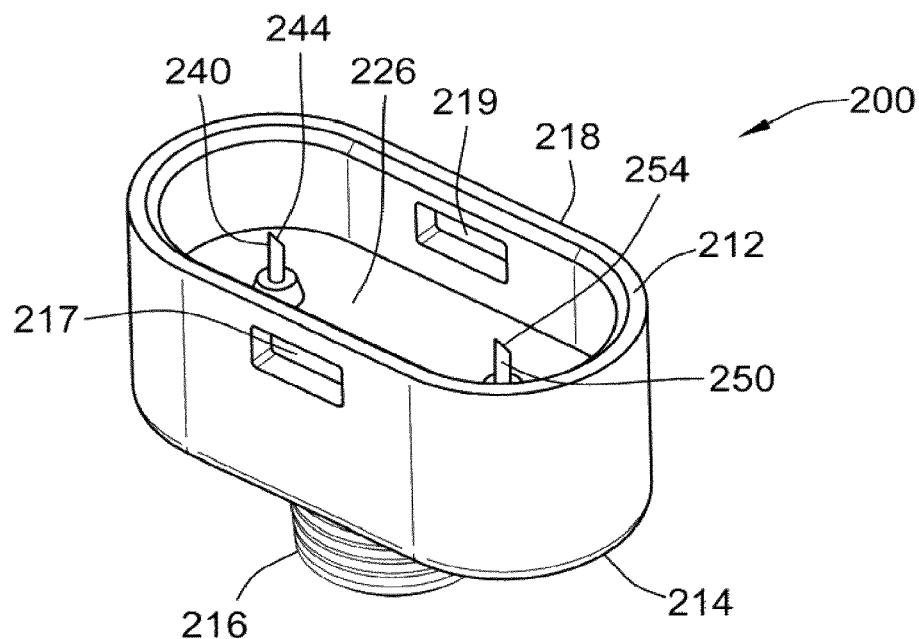
FIG. 8 illustrates another perspective view of the dispense interface illustrated in FIG. 4.
Figure 9:
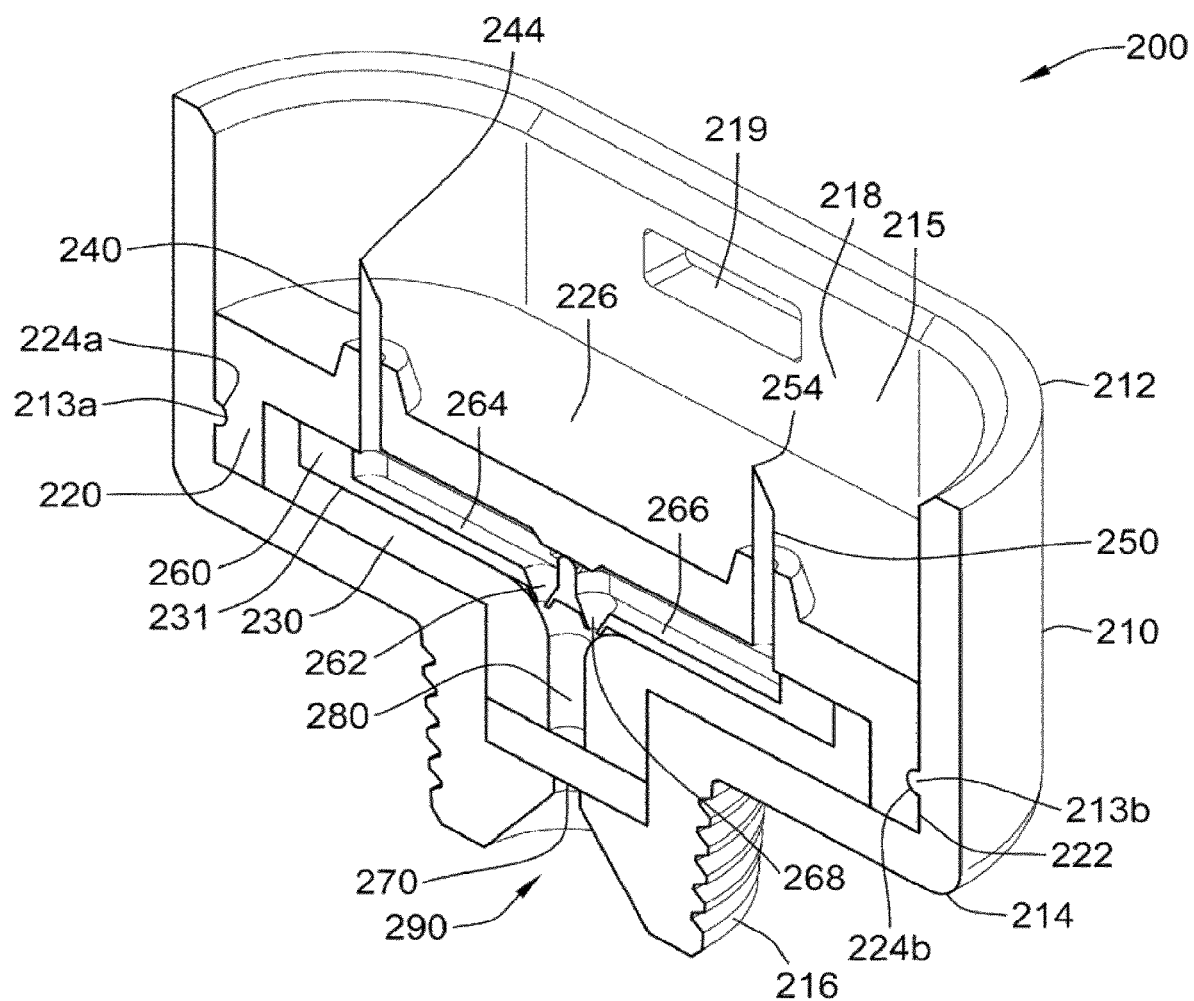
FIG. 9 illustrates a cross-sectional view of the dispense interface illustrated in FIG. 4.
Figure 10:
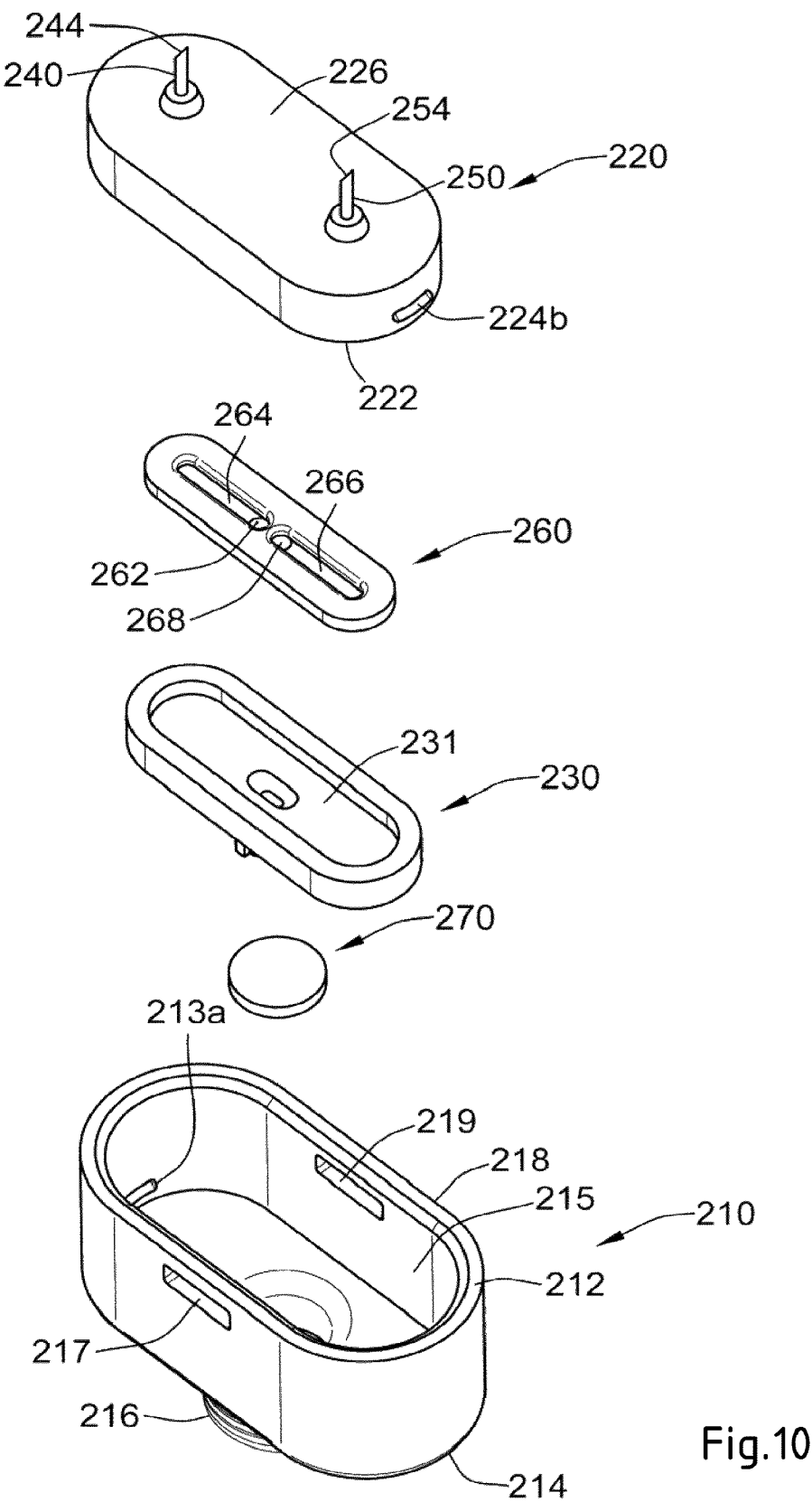
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
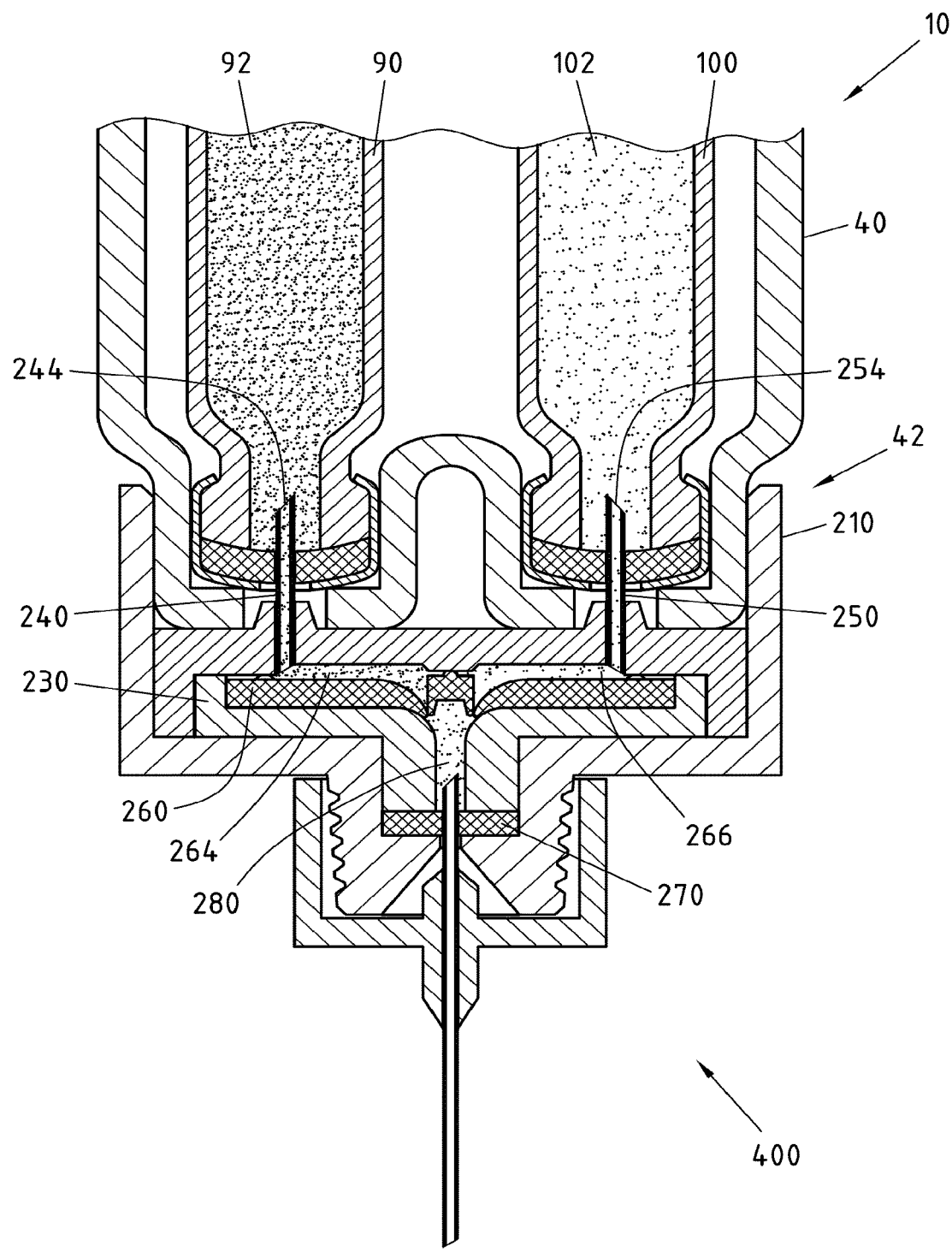
FIG. 11 illustrates a cross-sectional view of the dispense interface and dose dispenser mounted onto a drug delivery device, such as the device illustrated in FIG. 1.
Figure 12:
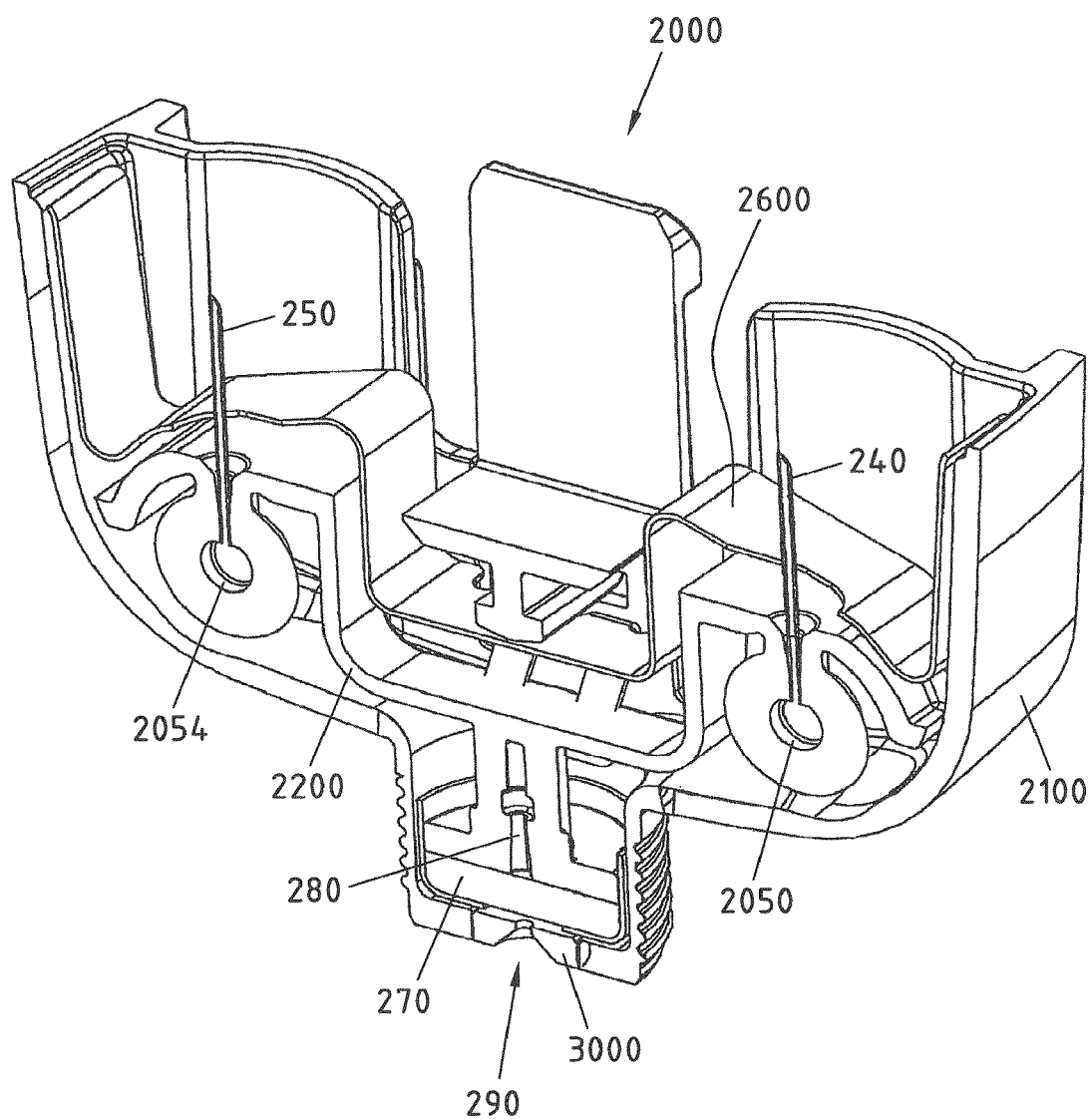
FIG. 12 illustrates a cross-sectional view of an alternative embodiment of a dispense interface.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

FIGS. 12 to 16 illustrate an embodiment of a dispense interface 2000 alternative to the embodiment of the dispense interface 200 illustrated in FIGS. 7 to 11. In FIGS. 12 to 16 the same reference signs as in FIGS. 7 to 11 are used for parts which may be similar. Furthermore, at this point, it is mainly referred to the above description of the embodiment of the dispense interface 200 illustrated in FIGS. 7 to 11 and, basically, the differences are described only.

As will now be discussed in greater detail, in one preferred arrangement, the dispense interface 2000 illustrated in FIGS. 12 to 15 comprises:

a. a main outer body 2100;
   b. an inner body 2200;
   c. a manifold 2300;
   d. a first piercing needle 240;
   e. a second piercing needle 250;

f. a lock-out spring 2600;
g. a first diaphragm valve 2700;
h. a second diaphragm valve 2750;
i. a ferrule 2800;
j. an outer septum 270; and
k. a needle guide 3000.

One exemplary difference between the dispense interface 200 and the dispense interface 2000 is the outer shape. In particular, the dispense interface 2000 is attachable to a drug deliver device by axial attachment means as described above and at least partially insertable in the drug delivery device. For instance, once the dispense interface 2000 is attached to the distal end of the drug delivery device, the distal end of the main body of the drug delivery device covers a portion of the dispense interface 2000.

One further exemplary difference between the dispense interface 200 and the dispense interface 2000 is the manifold 2300, which resides on the inner body 2200 such that a "Y"-shaped fluid channel is formed between the facing surfaces of the manifold 2300 and the inner body 2200.

The function of the first and second diaphragm valve 2700, 2750 of the dispense interface 2200 may basically relate to the function of the first and second non return valve 262, 264 of the dispense interface 200. As described above, such a valve arrangement may for instance be constructed so as to prevent back flow and/or cross contamination of the first and second medicaments contained in the first and second reservoirs, respectively.

Furthermore, the dispense interface 2000 comprises a dispense interface lockout element in the form of a lockout spring 2600. One reason that a lock out member may be incorporated into a dispense interface, such as the interface 2000, is to ensure that once the dispense interface is removed from the drug delivery device, the dispense interface cannot be reattached and used a second time. Preventing re-attachment tends to ensure that medicament is not allowed to reside in the dispense interface 2000 indefinitely and contaminate the drug delivered to the patient.

The ferrule 2800 may basically serve for holding the outer septum 270; and the needle guide 3000 of the dispense interface 2000 may basically serve for centering a proximal end of a needle assembly before piercing the outer septum 270.

Figure 14:
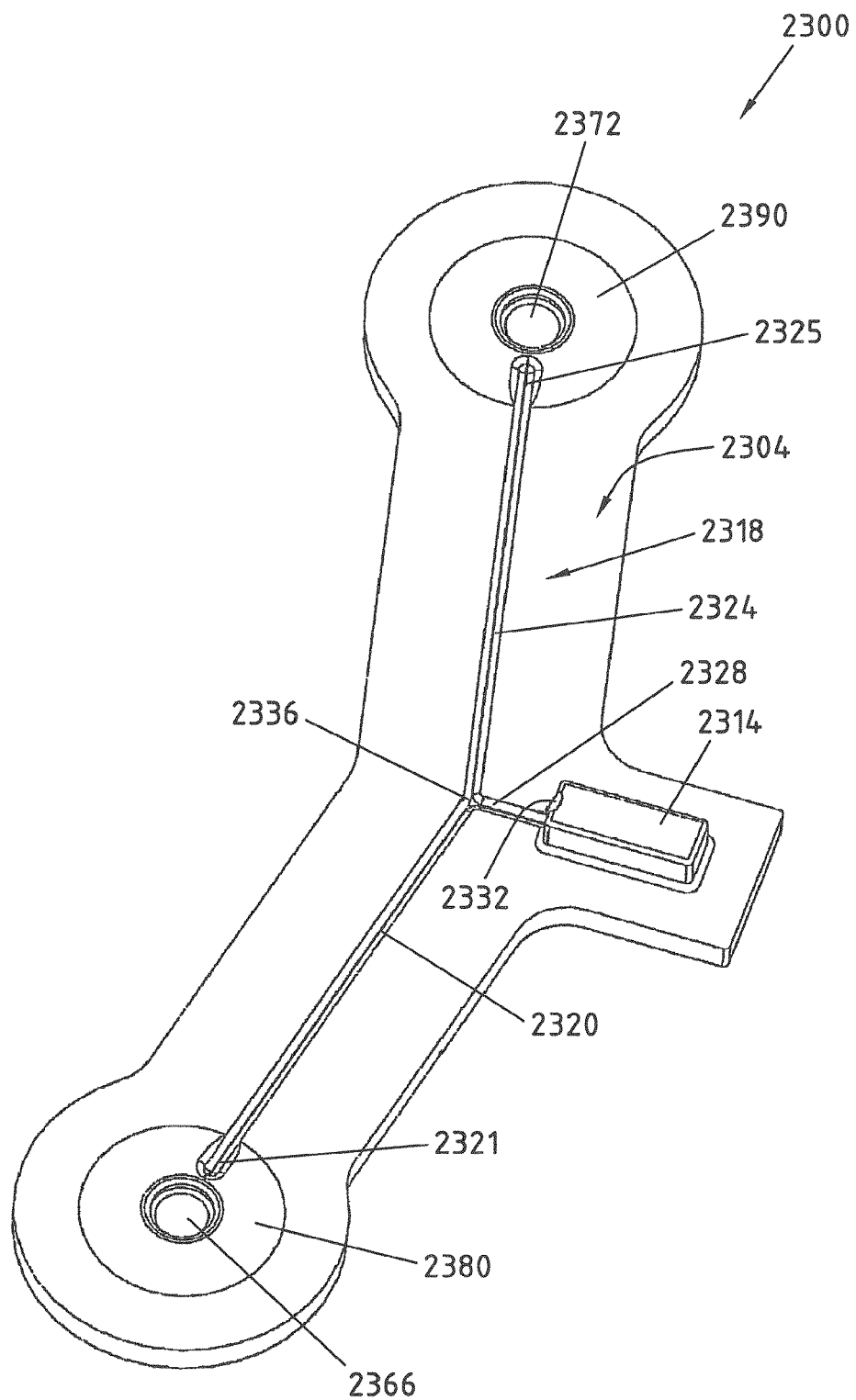
FIG. 14 illustrates a manifold of a dispense interface such as the alternative embodiment of the dispense interface illustrated in FIG. 12.

As illustrated in FIG. 14, the manifold 2300 comprises a first valve cavity 2366 and a second valve cavity 2372 provided along its top surface 2304. These cavities 2366, 2372 may be substantially flat and circular. The first valve cavity 2366 is configured to receive a circular protrusion 2710 of a first diaphragm 2700. Similarly, the second valve cavity 2372 is shaped for receiving a circular protrusion 2760 of a second diaphragm 2750.

Figure 13:
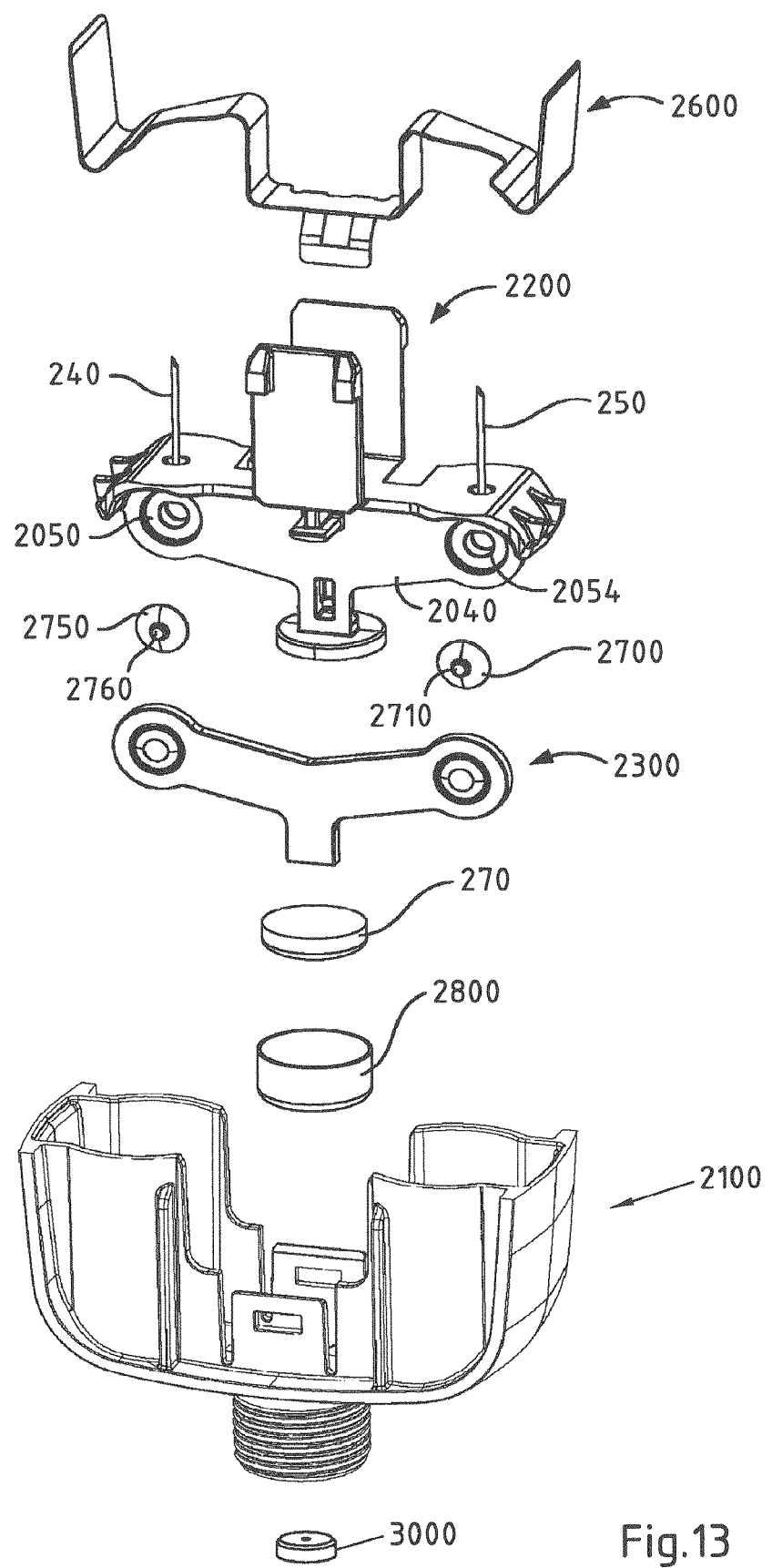
FIG. 13 illustrates an exploded of the alternative embodiment of a dispense interface illustrated in FIG. 12.

For example, in the exploded view illustrated in FIG. 13, alternative perspective views of both the first diaphragm 2700 and the second diaphragm 2750 are provided. As can be seen from these exploded view, the first diaphragm valve 2700 comprises a generally convex shape and comprises a circular protrusion 2710 near the apex of this convex shape. Similarly, the second diaphragm valve 2750 comprises a generally convex shape and comprises a circular protrusion 2760 near the apex of this convex shape.

In a preferred arrangement of the dispense interface 2000, the manifold surface is positioned to reside along the generally flat surface 2040 of the inner body 2200. Preferably, in order to provide a seal between the manifold and the inner body 2200, these two components may be laser welded together. In order to facilitate such a laser welding seal, in one arrangement, the inner body 2200 may be molded of Cyclo Olefin Polymer ("COP") material that is preferably doped with a laser welding additive. Such a laser welding additive may increase the inner body's sensitivity to laser light. In addition, the manifold 2300 may be moulded in an optically clear COP so as to allow the welding laser to pass through the manifold 2300 and activate a mating surface area residing between the two components with minimal interference. For instance, the surfaces 2304 and 2040 of the inner body 2200 and the manifold 2300, respectively, are joined at a joining area (e.g. the mating surface area and or a part of the mating surface area) defined by a laser welding track.

Figure 16:
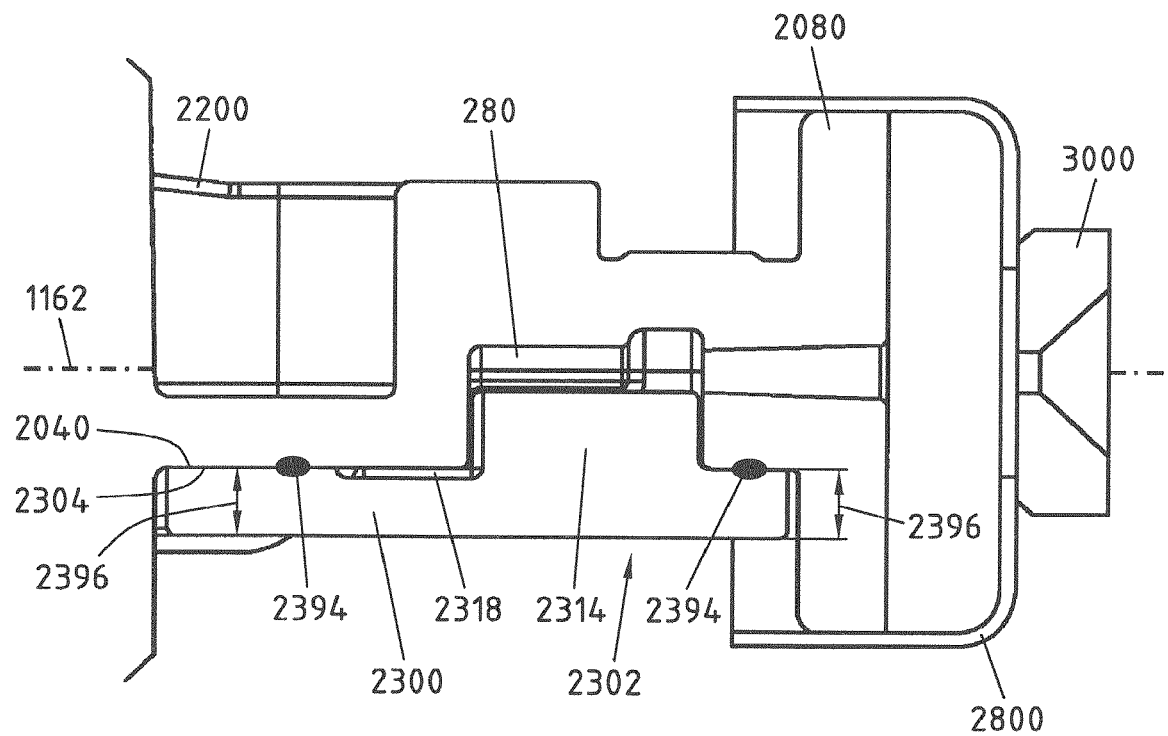
FIG. 16 illustrates a cross-sectional view of a manifold and an inner body of a dispense interface such as the alternative embodiment of the dispense interface illustrated in FIG. 12 joined by laser welding.
Figure 17:
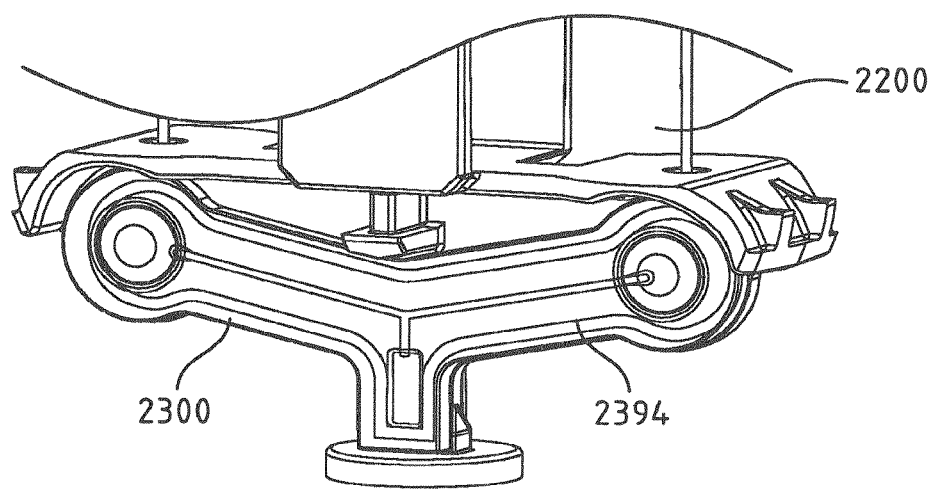
FIG. 17 illustrates a manifold and an inner body of a dispense interface such as the alternative embodiment of the dispense interface illustrated in FIG. 12 joined by laser welding.

For example, FIGS. 16 and 17 illustrates the manifold 2300 provided along the flat surface of the inner body and then laser welded along a laser welding track 2394. As shown, this laser welding track 2394 extends along an outer edge of the manifold 2300. The large, flat mating surface area of the surfaces 2304, on the manifold and the inner body 2040 respectively, help to produce substantial surface areas for the welding to act upon and this tends to maximize the seal created between these two components.

In particular, the laser welding track 2394 is closed and extends along a substantially flat area of the surfaces 2304 and 2040 of the manifold and the inner body respectively. Furthermore, FIG. 16 illustrates a partial sectional view of the manifold 2300 laser welded to the inner body 2200. As illustrated in FIG. 16, the thickness 2396 of the manifold 2300 at the laser welding track 2394 is substantially uniform. This is inter alia advantageous to ensure a constant laser welding spot at the joining area defined by the laser welding track and a constant focal length of the welding laser.

Preferably, the manifold 2300 further comprises a fluid groove arrangement 2318 and a rectangular protrusion or filling block 2314. As illustrated, referring to FIGS. 14 to 16, both the groove arrangement 2318 and the protrusion or filling block 2314 may be provided along a manifold top surface 2304. The protrusion 2314 may be provided near a distal end 2302 of the manifold 2300. In one preferred arrangement, this protrusion 2314 comprises a rectangular protrusion. With such a rectangular configuration, once the manifold 2300 is assembled (e.g., laser welded) along the flat surface 2040 of the inner body 2200, the protrusion 2314 will reside within the third cavity or holding chamber 280 of the inner body 2200. As illustrated, the rectangular protrusion or the filling block fills the majority of the third cavity or holding chamber while still redirecting fluid flow. One advantage of such a configuration is that it reduces the ullage of the dispense interface 2000. In addition, forming the fluid groove arrangement 2318 as a cavity between the two laser welded components allows the majority of the fluid groove geometry to be moulded using an open-and-shut tool. Consequently, use of an open-and-shut tool reduces the need for fragile core pins or split lines with the fluid groove arrangement. This also allows for relatively complex and tight tolerance geometry without complex tooling. The molding of key assembly snap features on the same component, such as an outer protrusion on the inner body 2200, also helps reduce tolerance stack-ups and also tends to allow for small needle wells and therefore smaller ullage.

In addition, the use of the needle guide 3000 to direct a Type A cannula means that the channel into which the cannula is received can be smaller as some of the tolerances on the needle position are reduced. The alignment of the flow path through the dispense interface also requires certain special considerations. In one example arrangement, both of the cartridges contained within the drug delivery device as well as the needle assembly are positioned in a single plane cutting through the depth of the drug delivery device along the longitudinal device centerline 1162. Furthermore, the longitudinal axis of the first and second piercing needles 240, 250 forming the inlet of the diaphragm valve 2700, 2750 and the first and second reservoir 2050, 2054 may be positioned in this single vertical plane. However, due to the positioning of the diaphragm valves 2700, 2750 and the fluid groove arrangement 2318 on one side of the dispense interface components, the fluid groove arrangement 2318 is moved off this centerline 1162. In particular, the diaphragm valves 2700, 2750 may be arranged such that they may provide a fluid seal between the first and second reservoir 2050, 2054, respectively, and the fluid groove arrangement 2318. Accordingly, the diaphragm valves 2700, 2750 may be arranged in another vertical plane spaced from and parallel to the single plane cutting through the depth of the drug delivery device along the longitudinal device centerline 1162. Also, the fluid groove arrangement 2318 forming the outlet of the diaphragm valves 2700, 2750 may be arranged in another single vertical plane spaced from and parallel to the single plane cutting through the depth of the drug delivery device along the longitudinal device centerline 1162.

The vertical arrangement of the diaphragm valves 2700, 2750 and the fluid groove arrangement 2318 in the dispense interface 2000 is inter alia advantageous to allow the manifold and the inner body to be joined by a laser positioned angled (e.g. perpendicular) to the first vertical plane cutting through the depth of the drug delivery device along the (longitudinal) device centerline 1162. Positioning the laser angled (e.g. perpendicular) to the first vertical plane is inter alia advantageous, because from such a horizontal position the laser may only need to pass through the manifold which may have an at least substantially uniform thickness at the laser welding track, whereas from a vertical position the laser may need to pass through additional components having no uniform thickness at the laser welding track. In other words, this vertical arrangement of the diaphragm valves 2700, 2750 and the fluid groove arrangement is inter alia advantageous to allow the body part and the cover part to be joined by laser welding at a joining area of the vertically oriented surfaces 2304, 2040 which is easily accessible by a laser.

Prior to dispense through an attached needle assembly, the groove arrangement 2318 is brought back onto the centerline 1162 using the third cavity or holding chamber 280 molded into the inner body 2200. These factors combine to reduce the volume of liquid or medicament required to fill the dispense interface 1200 prior to dispense, thereby aiding dose accuracy.

Returning to the perspective view of the manifold 2300 provided by FIG. 14, preferably, the first valve cavity 2366 is positioned in the center of a first convex protrusion 2380 situated along the top surface 2304 of the manifold 2300. In such an arrangement, when the circular protrusion 2710 of the first diaphragm valve 2700 is seated within the first valve cavity 2366, the diaphragm valve 2700 provides a fluid seal between the first circular recess or reservoir 2050 defined by the inner body 2200 and the fluid groove arrangement 2318 provided along the top surface of the manifold 2300. However, if fluidic pressure is applied upon the first diaphragm valve 2700 (e.g., during a dose priming or a dose injecting step), the first valve 2700 will change from an un-stressed state to a stressed state. In the stressed state, fluidic pressure inverts the naturally convex shape of the first valve 2700 so that the convex nature of the first valve inverts and thereby will reside along a top surface of the first convex protrusion 2380. In this stressed condition, the first diaphragm valve 2700 will allow fluid to flow from the first reservoir of the inner body 2200 and the fluid groove arrangement 2318 of the manifold 2300.

Similarly, the second valve cavity 2372 is also shaped for receiving a circular protrusion 2760 of a second circular diaphragm valve 2750. Moreover, this second valve cavity 2372 is also positioned near an apex of a second convex protrusion 2390. The second diaphragm valve operates in a similar manner as the first diaphragm valve when fluid pressure is applied.

As will be explained in greater detail below, it is the operation of a first and second diaphragm valves 2700, 2750 along with a fluid groove arrangement 2318 that allows the first and second reservoirs 2050, 2054 of the inner body 2200 to be used for priming and dose administration of the first and/or second medicaments contained within a multiple medicament drug delivery device, such as the device illustrated in FIG. 1.

Figure 15:
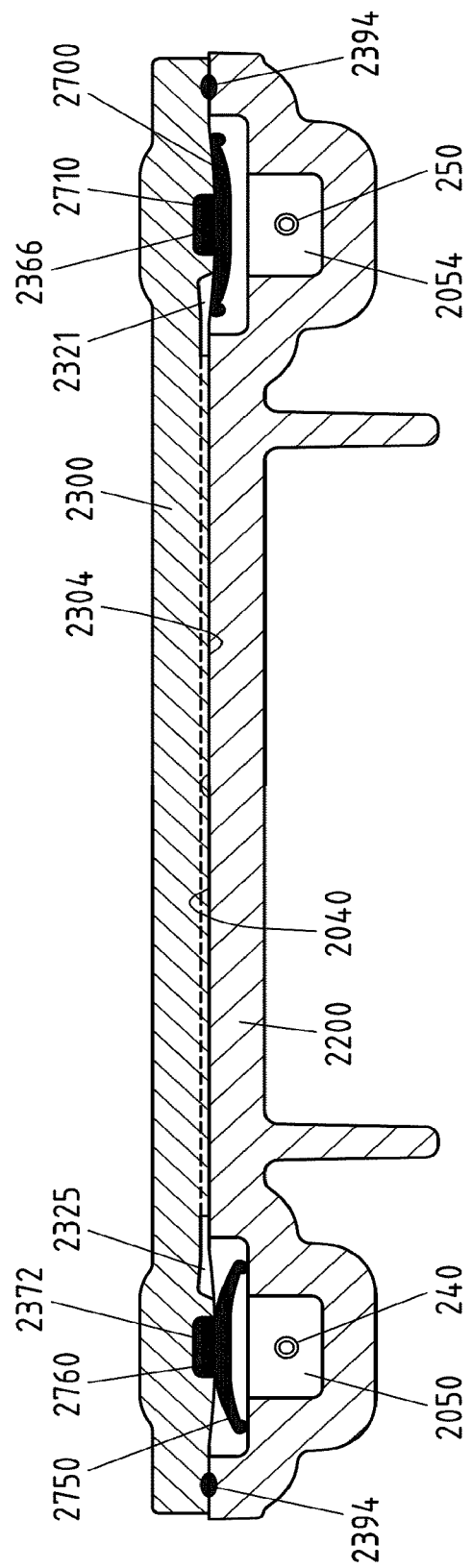
FIG. 15 illustrates a schematic cross-sectional view of diaphragm valves arranged between a manifold and an inner body of the dispense interface illustrated in FIG. 12 joined by laser welding.

As described above, the presently disclosed dispense interface 2000 may comprise a valve arrangement comprising a first and a second diaphragm valve 2700, 2750. One advantage of utilizing such diaphragm or umbrella valves 2700, 2750 is that they characteristically tend to have low cracking or opening pressure. Another advantage of such valve structures is that they tend to provide low or minimal resistance to flow when open and they also tend to seal effectively against back pressure. These valves can also be designed to be very small in size, for example, on the order of approximately 3.5 mm to about approximately 4.5 mm. As such, these valves can tend to minimize the post valve ullage within the dispense interface 2000. However, other valve arrangements may also be utilized for the dispense interface 2000. In FIG. 15 a schematic cross-sectional view of the diaphragm valves 2700, 2750 arranged between the manifold 2300 and the inner body 2200 of the dispense interface 2000 is illustrated.

For example, a first fluid groove 2320 is provided along the manifold top surface 2304. This first fluid groove 2320 has a starting point 2321 near the first valve cavity 2366 but this first fluid groove 2320 is not in fluid communication with this first cavity. Similarly, a second fluid groove 2324 has a starting point 2325 near the second valve cavity 2372 but is not in fluid communication with this second cavity. As illustrated in FIG. 14, the first and second fluid grooves 2320, 2324 may be configured to meet near an intersection 2336 along the flat surface, near the middle of the T-shaped manifold 2300. At this intersection 2336, the first and second grooves 2320, 2324 meet at a third fluid groove 2328. This third groove 2328 resides in fluid communication with a fourth fluid groove 2332. In one preferred arrangement, this fourth fluid groove 2332 may be provided along an external surface of the rectangular protrusion 2314 provided along the bottom surface of the manifold 2300. As such, when the top surface 2304 of manifold 2300 is positioned along the generally flat surface 2040 of the inner body 2200 and then laser welded, the manifold 2300 and these plurality of fluid grooves 2320, 2324, 2328, and 2322 (i.e. fluid groove arrangement 2318) allow for fluid communication between the first and second reservoirs 2050, 2054 of the inner body 2200 and the holding chamber of the inner body 2200.

In addition, the substantially flat bottom surface of the manifold 2300 further comprises a first convex protrusion 2380 and a second convex protrusion 2390. Preferably, the first protrusion 2380 comprises a generally convex shape and further defines the first valve cavity 2366. Similarly, the second convex shaped protrusion defines the second valve cavity 2372. As will be described in greater detail below, when the top surface of the manifold 2300 is assembled along the flat surface of the inner body 2200, a first diaphragm valve protrusion is placed within this first circular shaped cavity and a second diaphragm valve protrusion will be placed within this second circular shaped cavity.

In the exemplary view of FIG. 15, the diaphragm valve 2700 is shown in a stressed state and the diaphragm valve 2750 is shown in a non-stressed state. Since the first and second diaphragm valves have a generally convex shape in a non-stressed position, in a non-stressed state, the convex nature of the diaphragm valve will provide a sealing arrangement between the manifold and the inner body so as to prevent any fluid from flowing from the first cavity of the inner body, through the first groove and into the holding chamber. However, in a stressed or non-steady state where pressure is exerted upon the convex diaphragm valves, the valve will come under stress and the unstressed convex nature of the diaphragm valve will be inverted, such that the valve will fold back towards the convex protrusion of the manifold. In this stressed position, the valve will therefore allow for fluid communication between the inner body first reservoir and the start portion of the first fluid groove which will then move towards the holding chamber by way of the third groove 2328 and also the fourth groove 2332 of the manifold. The second diaphragm valve operates in a similar manner to allow fluid to flow from the second reservoir of the inner body to the holding chamber of the inner body.

Even in the non-stressed state, the edges of the valve may exert a certain pressure on the housing in order to provide a tight sealing or closure of the starting points 2321, 2325 of the fluid grooves 2320, 2324.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(o>carboxyheptadecanoyl)-des(B30) human insulin and B29-N-(co-carboxyhepta-decanoyl) human insulin.

Exendin-4 for example means Exendin-4(1-39), a peptide of the sequence HHis-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pr37 Exendin-4(1-39)-NH2,
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Trp(O2)25] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two P sheets create a "sandwich" shape, held together by interactions between conserved cysteines and other charged amino acids.

There are five types of mammalian Ig heavy chain denoted by a, 8, 8, y, and (i. The type of heavy chain present defines the isotype of antibody; these chains are found in IgA, IgD, IgE, IgG, and IgM antibodies, respectively.

Distinct heavy chains differ in size and composition; a and y contain approximately 450 amino acids and 8 approximately 500 amino acids, while (i and 8 have approximately 550 amino acids. Each heavy chain has two regions, the constant region (CH) and the variable region (VH). In one species, the constant region is essentially identical in all antibodies of the same isotype, but differs in antibodies of different isotypes. Heavy chains y, a and 8 have a constant region composed of three tandem Ig domains, and a hinge region for added flexibility; heavy chains (i and s have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by X and K. A light chain has two successive domains: one constant domain (CL) and one variable domain (VL). The approximate length of a light chain is 211 to 217 amino acids. Each antibody contains two light chains that are always identical; only one type of light chain, K or X, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted CI C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

We claim:

1. A medical device configured to eject a medicament, the medical device comprising:
    a body part defining an inner body of the medical device; and
    a cover part defining a manifold of the medical device, wherein the body part and the cover part are configured and dimensioned to at least partially form a fluid channel between a first surface of the body part and a first surface of the cover part, wherein the first surface of the body part and the first surface of the cover part are joined to each other and are at least substantially flat at a joining area that connects the body part and the cover part, and wherein the joining area is at least substantially parallel to a longitudinal axis of the medical device.

2. The medical device according to claim 1, wherein the body part comprises:
    a recess; and
    at least one body part reservoir, wherein the fluid channel is configured to provide a fluid connection from the at least one body part reservoir to the recess.

3. The medical device according to claim 2, wherein the at least one body part reservoir is configured to receive a diaphragm valve such that the diaphragm valve is substantially arranged in a first plane parallel to the longitudinal axis of the medical device.

4. The medical device according to claim 1, wherein the body part comprises a groove arrangement in the first surface of the body part.

5. The medical device according to claim 1, wherein the cover part comprises a groove arrangement arranged in the first surface of the cover part.

6. The medical device according to claim 1, wherein the body part, the cover part, or both are formed by moulding.

7. The medical device according to claim 1, wherein the body part, the cover part, or both are formed from a Cyclo Olefin Polymer material.

8. The medical device according to claim 1, wherein the first surface of the body part and the first surface of the cover part are joined by laser welding at the joining area.

9. The medical device according to claim 8, wherein the body part, the cover part, or both are at least partially formed from a material that is at least substantially transparent to radiation of a welding laser used to laser weld the joining area.

10. The medical device according to claim 9, wherein a thickness of the body part measured perpendicular to the first surfaces at the joining area, a thickness of the cover part measured perpendicular to the first surfaces at the joining area, or both are at least substantially uniform over the joining area.

11. The medical device according to claim 8, wherein the body part, the cover part, or both are at least partially formed from a material doped with a laser welding additive.

12. The medical device according to claim 1, wherein the body part includes an inner body forming a first body part reservoir and a second body part reservoir;
    wherein the cover part defining the manifold is positioned adjacent the inner body and comprising a fluid groove; and
    wherein the medical device further comprises:
        a first piercing needle in fluid communication with the first body part reservoir;
        a second piercing needle in fluid communication with the second body part reservoir; and
        a lockout element.

13. A method comprising:
    manufacturing a medical device according to claim 1, the manufacturing comprising:
    moulding the body part, the cover part, or both; and
    joining by laser welding the first surface of the body part and the first surface of the cover part at the joining area.

14. A dispense interface attachable to a drug delivery device to form a medical device configured to eject a medicament, the dispense interface comprising:
    a body part defining an inner body of the dispense interface; and
    a cover part defining a manifold of the dispense interface, wherein the body part and the cover part are configured and dimensioned to at least partially form a fluid channel between a first surface of the body part and a first surface of the cover part, wherein the first surface of the body part and the first surface of the cover part are joined to each other and are at least substantially flat at a joining area that connects the body part and the cover part, and wherein the joining area is configured to be at least substantially parallel to a longitudinal axis of the medical device when the dispense interface is attached to the drug delivery device to form the medical device.

15. A method for manufacturing a dispense interface according to claim 14, the method comprising:
    molding the body part, the cover part, or both; and
    joining by laser welding the first surface of the body part and the first surface of the cover part at the joining area.

* * * * *